(12) United States Patent
Lovett

(10) Patent No.: US 10,733,904 B2
(45) Date of Patent: Aug. 4, 2020

(54) DEVICE FOR SPEECH ARTICULATION

(71) Applicant: Lauren Lovett, Studio City, CA (US)

(72) Inventor: Lauren Lovett, Studio City, CA (US)

( * ) Notice: Subject to any disclaimer, the term of this patent is extended or adjusted under 35 U.S.C. 154(b) by 183 days.

(21) Appl. No.: 15/689,270

(22) Filed: Aug. 29, 2017

(65) Prior Publication Data

US 2018/0061273 A1 Mar. 1, 2018

Related U.S. Application Data

(60) Provisional application No. 62/380,996, filed on Aug. 29, 2016.

(51) Int. Cl.
*G09B 19/04* (2006.01)
*A61F 5/58* (2006.01)
*A61B 5/00* (2006.01)

(52) U.S. Cl.
CPC .............. *G09B 19/04* (2013.01); *A61F 5/58* (2013.01); *A61B 5/4803* (2013.01)

(58) Field of Classification Search
USPC ............ 434/185, 263; 433/6; 606/234, 235; D24/194, 195
See application file for complete search history.

(56) References Cited

U.S. PATENT DOCUMENTS

| | | | | |
|---|---|---|---|---|
| 3,267,937 A * | 8/1966 | Verschoor | ............... | A61J 17/02 606/236 |
| 3,556,093 A * | 1/1971 | Quick | ...................... | A61F 5/58 600/24 |
| 3,690,324 A * | 9/1972 | Spivack | ................... | A61J 17/02 606/234 |
| 4,688,571 A * | 8/1987 | Tesler | .................. | A61J 17/001 606/234 |
| 4,759,453 A * | 7/1988 | Paetzold | .................... | A61J 9/00 215/11.1 |
| 4,934,534 A * | 6/1990 | Wagner | .................. | A45D 44/20 206/523 |
| 5,160,344 A * | 11/1992 | Werton | ................... | A61J 17/02 606/234 |
| 5,257,930 A * | 11/1993 | Blakeley | ............... | G09B 19/04 433/168.1 |
| 5,522,848 A * | 6/1996 | Kamali | ................. | A61J 17/005 606/234 |
| D375,793 S * | 11/1996 | Owen | ......................... | D24/195 |
| 5,606,871 A * | 3/1997 | Hansen | ..................... | F25D 3/08 606/235 |
| 5,782,868 A * | 7/1998 | Moore, Jr. | ............. | A61J 17/02 606/235 |
| 6,499,995 B1 * | 12/2002 | Schwartz | ................. | A61C 7/00 128/862 |
| 6,632,095 B2 * | 10/2003 | Ryan | .................... | A63B 23/032 434/185 |
| 6,660,029 B2 * | 12/2003 | VanSkiver | ............. | A61C 19/08 607/112 |
| 7,214,064 B1 * | 5/2007 | Hall | ....................... | G09B 19/04 434/185 |

(Continued)

*Primary Examiner* — Kurt Fernstrom
(74) *Attorney, Agent, or Firm* — Morris & Kamlay LLP

(57) ABSTRACT

A device is provided that includes a semi-rigid ring made of one or more non-toxic materials that is suitable for being placed in a speaker's mouth. The ring has an outer diameter in the range of 30-45 mm and an inner diameter in the range of 20-40 mm to allow for placement in a speaker's mouth while speaking.

16 Claims, 3 Drawing Sheets

(56) References Cited

U.S. PATENT DOCUMENTS

| | | | | |
|---|---|---|---|---|
| D581,540 S | * | 11/2008 | Nielsen | D24/194 |
| D697,274 S | * | 1/2014 | Thorne | D24/194 |
| D739,034 S | * | 9/2015 | Lee | D24/195 |
| D768,302 S | * | 10/2016 | Pauschitz | D24/195 |
| 9,883,988 B1 | * | 2/2018 | Kumbasi | A61J 17/008 |
| 2003/0205234 A1 | * | 11/2003 | Bardach | A61C 19/063 |
| | | | | 128/861 |
| 2006/0177793 A1 | * | 8/2006 | Crohn | A61B 1/24 |
| | | | | 433/29 |
| 2009/0112260 A1 | * | 4/2009 | Renko | A61J 17/02 |
| | | | | 606/235 |
| 2010/0016896 A1 | * | 1/2010 | Rosenthal | A44C 5/0084 |
| | | | | 606/235 |
| 2012/0045729 A1 | * | 2/2012 | Ortiz | A61C 7/00 |
| | | | | 433/6 |
| 2014/0296914 A1 | * | 10/2014 | Oneto | A61J 17/02 |
| | | | | 606/235 |
| 2016/0106631 A1 | * | 4/2016 | Rohrig | A61J 17/007 |
| | | | | 606/235 |
| 2016/0158658 A1 | * | 6/2016 | Lakritz | A63H 3/02 |
| | | | | 446/71 |

* cited by examiner

DEVICE FOR SPEECH ARTICULATION

CROSS-REFERENCE TO RELATED APPLICATIONS

This application is related to U.S. Application No. 62/380,996, filed Aug. 29, 2016, the disclosure of which is incorporated by reference in its entirety.

BACKGROUND

Traditional techniques for improving or refining speech often involve holding a small object, typically a cork, marble, or the like, in the speaker's mouth. For example, a speaker wishing to learn to speak more clearly may practice speaking with such an object positioned between the speaker's teeth or otherwise within the speaker's mouth. The speaker's mouth and speaking habits adjust to the presence of the object, thereby strengthening them. However, such techniques often are unreliable, prone to error, or ineffectual.

DETAILED DESCRIPTION

Embodiments disclosed herein provide a "speech ring," which is suitable for use as a personal articulation refinement tool, and techniques for using the same.

In contrast to conventional techniques for improving or refining speech, embodiments disclosed herein provide a device and technique to improve speech, for example to rehabilitate or improve general speech, improve the quality, efficiency, or other aspects of learning a particular language, accent, and/or style of speech, remove a regional accent, or the like.

Figure 1:
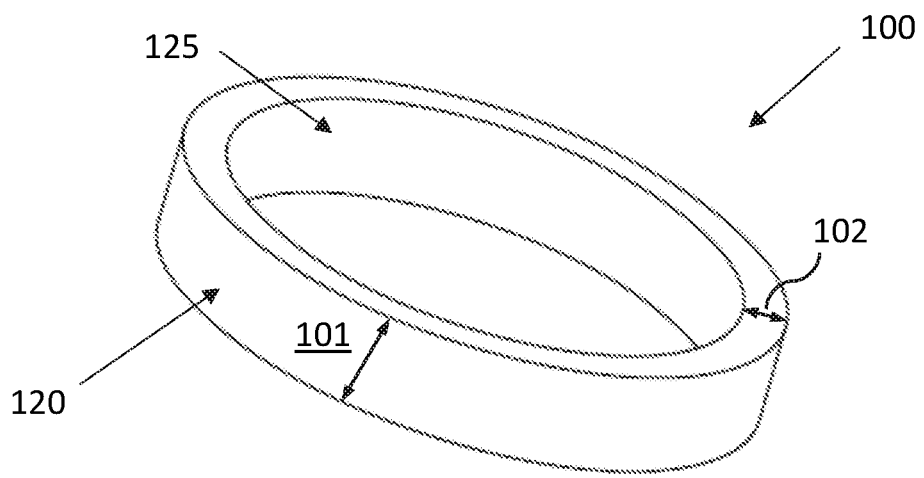
FIG. 1 shows a perspective view of a speech ring according to embodiments disclosed herein.

A speech ring as disclosed herein may be a torus-shaped or generally torus-shaped device that may be held in a speaker's mouth while learning or practicing various speech sounds. FIG. 1 shows an example perspective view of a speech ring 100. The speech ring 100 may be an ovoid torus, i.e., a ring having a circular or oval cross-section. In some embodiments, a speech ring may have a different cross-section, such as a rectangular cross-section as shown in FIG. 1, or an irregular or non-uniform cross-section. More generally, a speech ring as disclosed herein may have any generally ring-shaped configuration, with any cross-sectional profile.

Figure 2:
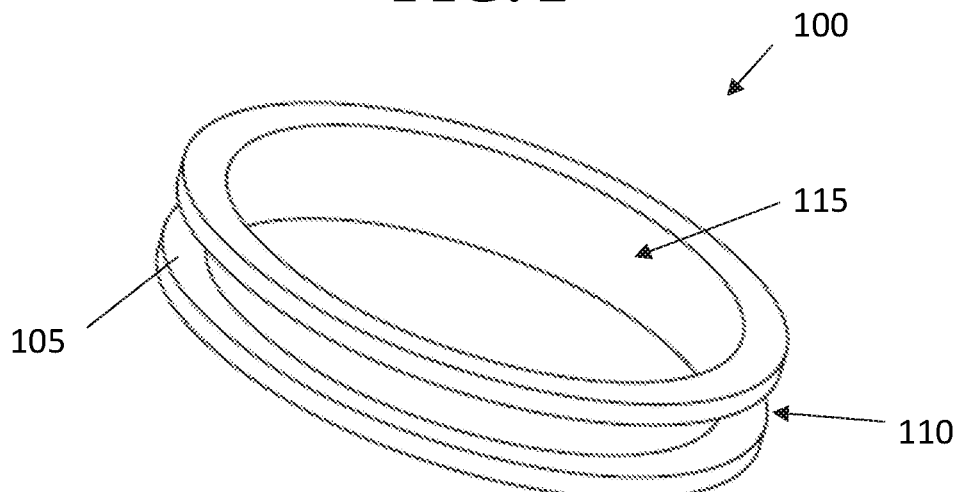
FIG. 2 shows a perspective view of a speech ring having a non-regular cross section according to embodiments disclosed herein.

In some embodiments, a speech ring as disclosed herein may include edge features disposed on the outer and/or inner surfaces of the ring. For example, FIG. 2 shows an embodiment in which a notch 105 is disposed around the outer surface 110 of the speech ring. Alternatively or in addition, a notch may be disposed around the inner edge 115 of a speech ring. Such a notch may have any shape. More generally, such surface features may be indentations such as the notch 105 or protrusions. The features may be uniform around the outer and/or inner edge of the ring, or they may be disposed in regular or irregular patterns around the edges. One or more edges 109 of the speech ring may be relatively sharp corners, such as from the intersection of two generally flat or planar surfaces, or they may be rounded or beveled and thus relatively smooth. It generally will be preferred for a speech ring as disclosed herein to have rounded or beveled edges, so as to be comfortable when placed in a speaker's mouth.

A speech ring as disclosed herein may have various dimensions. For example, in an embodiment a speech ring may have an outer diameter of 30-45 mm. The thickness 102 of a speech ring as disclosed herein may be in the range of about 3-6 mm. The height 101 of a speech ring as disclosed herein may be in the range of about 5-10 mm. A speech ring may have an inner diameter in the range of approximately 30-45 mm. A speech ring may have an outer diameter in the range of about 30-45 mm. Generally, it may be preferred for the inner portion of the ring to be sufficiently large that a speaker's tongue may move relatively unimpeded through the ring during normal speech. In some embodiments, different sizes may be suitable for different sizes of speakers' mouths. For example, a relatively smaller ring may have an outer diameter of about 30-35 mm and an inner diameter of 22-27 mm. A specific embodiment provides a speech ring having a thickness of about 4 mm, a height of about 7 mm, and an outer diameter of about 32.5 mm. A relatively larger ring, which may be preferred for a speaker with a larger mouth, may have an outer diameter in the range of about 40-44 mm and an inner diameter of about 30-34 mm. A specific embodiment provides a speech ring having a thickness of about 5 mm, a height of about 7 mm, and an outer diameter of about 42 mm. Other dimensions may be used. For example, a speech ring as disclosed herein may have an outer diameter in the range of 1.1 to 1.7 inches and an inner diameter in the range of 0.9 to 1.3 inches. In an example embodiment, a speech ring as disclosed herein may have an outer diameter of 1.25±0.05 inches and an inner diameter of 1.00±0.05 inches. In another example embodiment, a speech ring may have an outer diameter of 1.625±0.05 inches and an inner diameter of 1.25±0.05 inches.

Various example embodiments as disclosed herein may be preferred in different use scenarios, as they provide speech rings that are properly sized for a relatively wide variety of human mouths without requiring adjustment or individual fitting for each speaker.

A speech ring may be uniform in thickness, cross-sectional shape, and the like, or may have varying physical dimensions, such as to fit a particular speaker's mouth. In some embodiments, a speech ring may be custom-fitted to a particular speaker's mouth, in which case the specific dimensions of the ring may be determined based upon a measurement of the speaker's mouth, tongue, teeth arrangement, and the like.

In some embodiments, the speech ring may have a non-uniform cross-sectional shape, such as to make it easier for a speaker to determine how the ring should be placed in the speaker's mouth. For example, half of a speech ring may be beveled on a portion of the inside and/or a portion of an outer surface of a speech ring may be edged. A speaker may thus be able to immediately determine by feel how the ring should be positioned within the speaker's mouth. Such non-uniformity also may allow a speaker to identify when the ring has shifted within the speaker's mouth, without requiring the ring to be removed from the mouth. For example, referring to FIG. 1, the visible portion 120 of the outer surface of the speech ring may include a bevel, edge, or other discernable surface treatment that can be distinguished from the other surfaces of the ring by feel. The remainder of the ring may have the same, uniform surface treatment. For example, the remainder of the ring may be smooth to the touch. The surface treatment portion 120 may be half, less than half, or more than half of the relevant surface of the speech ring. For example, only a portion of the outer surface 120 and/or only a portion of the inner surface 125, less than the entire surface, may have such a surface treatment.

It generally may be preferred for a speech ring as disclosed herein to be semi-rigid. An entirely rigid ring, such as one formed from rigid plastic, metal, or the like, would not allow for deformation of the ring when placed in a speaker's mouth. Such a ring would be uncomfortable for the speaker, and likely would not provide a benefit to the speaker in improving the accuracy, intelligibility, or the like of the speaker's speech. However, it generally is desired for a speech ring as disclosed herein to provide sufficient rigidity that it affects the user's speech and increases the strength and finesse of a speaker's facial muscles to obtain the benefits disclosed herein. Thus, it may be preferred for a speech ring to be semi-rigid, i.e., not entirely rigid, but providing sufficient resistance to alter a speaker's speech. In some embodiments, a speech ring may be formed from materials having a Young's modulus of less than 10, more preferably less than 5. Similarly, it may be preferred for the material to have a Young's modulus of at least 1.

In some embodiments, the dimensions of the speech ring may be partially determined by the particular material or materials used to fabricate the ring. In general, the firmness of the speech ring will be determined by the thickness of the ring (i.e., the diameter of the cross-section) and by the material used. If the ring is too rigid, it may be uncomfortable or may not yield sufficiently to movements of the speaker's mouth to achieve the desired effects. Similarly, if the ring is too thin then it may collapse during use by a speaker and thus be unable to provide the desired benefits. Thus, although the dimensions disclosed herein are suitable for use with the materials disclosed herein, other dimensions and materials may be used to achieve a similar ridigity.

A speech ring as disclosed herein may be formed from any suitable non-toxic material. As used herein, a "non-toxic material" is one that is considered safe and non-harmful to place in a person's mouth while the person is speaking. In some embodiments, it may be preferred for a speech ring as disclosed herein to be made from a non-BPA and/or non-plastic acrylic or other similar material. As a specific example, Talon™, available from Talon Acrylics, Inc. of Winchester, Oreg., may be used. As another specific example, a thermoplastic nylon or resin, such as TCS unbreakable nylon available from Thermoplastic Comfort Systems, Inc. may be used. It may be preferred that the material be suitable for use in injection molding processes to allow for efficient fabrication. A speech ring may be fabricated of a single material, or a combination of two or more suitable materials as disclosed herein. Preferably, the material may be relatively pliant such that it shapes to a speaker's mouth during use, while retaining the capability of being re-shaped after use. For example, a speech ring may be re-shaped to an original approximately circular configuration by applying heat such as via warm water during cleaning, by being placed into an appropriately-shaped container, or the like. It may be preferred for a speech ring as disclosed herein to be cleanable using warm water and/or conventional soap.

Figure 3A:
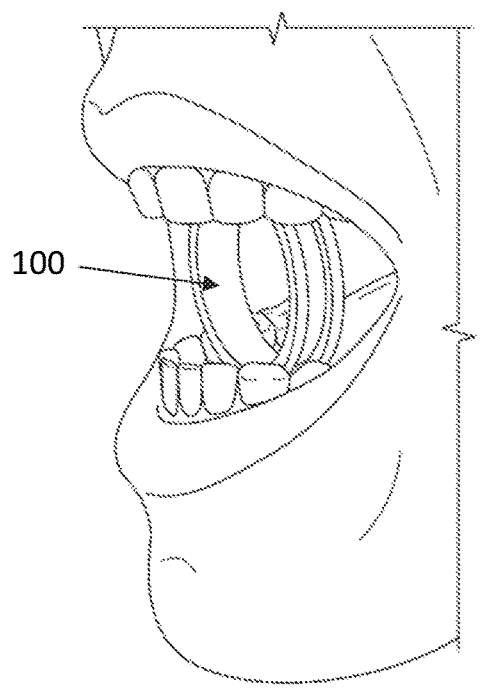
FIG. 3A shows an example of a speech ring disposed within the mouth of a speaker according to embodiments disclosed herein.
Figure 3B:
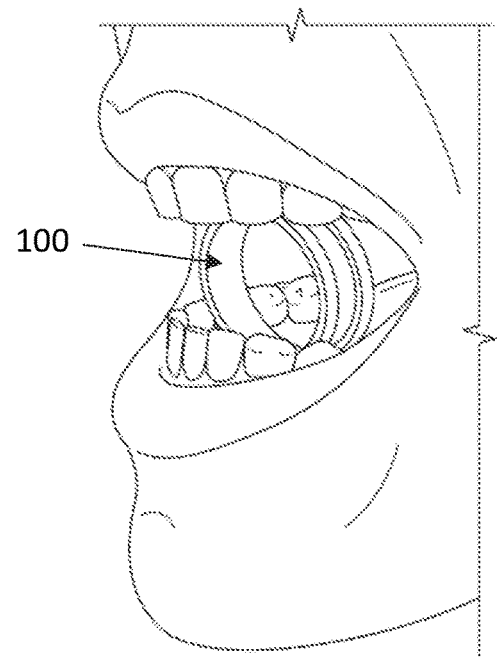
FIG. 3B shows an example of a speech ring disposed within the mouth of a speaker while the speaker is speaking, according to embodiments disclosed herein.

FIGS. 3A and 3B show an example of a speech ring as disclosed herein in use by a speaker. FIG. 3A shows the ring initially placed in the speaker's mouth. FIG. 3B shows the ring during use, for example, while the speaker is speaking. As shown, the ring may deform slightly during use, while still providing resistance to movement of the speaker's jaw. During use, the speech ring 100 may be placed within a speaker's mouth. When the speaker forms speech sounds, the ring may cause improved engagement and strengthening of the facial muscles, tongue, and breathing, while allowing the speaker's tongue to move relatively freely within the speaker's mouth, thereby improving the accuracy of the speaker at forming the speech sounds. One benefit of a speech ring as disclosed herein in contrast to conventional devices as previously disclosed may be that the speech ring allows the speaker's tongue to rest within or move freely within the speech ring, thus preventing undesirable obstruction of tongue movement that could counteract the beneficial resistance provided by the ring. When the speaker repeats the same or similar speech after removing the speech ring, the speaker then may be able to form the same or similar sounds more easily and clearly, thereby improving the speaker's speech. In many cases, no particular training may be required for a speaker to gain the benefit of a speech ring as disclosed herein, as the benefits may be obtained due to the mere presence of the speech ring in the speaker's mouth during regular speech. Alternatively or in addition, a speaker may perform specific speaking exercises using the speech ring to further enhance or improve the benefits deriving therefrom.

A speech ring as disclosed herein also may be used, for example, for diagnostic and adjustment during and/or after dental or facial surgery, or the like, in some cases in a similar fashion to the sue of a "bone prop." For example, when false teeth or other dental appliances are placed in a speaker's mouth, the use of a speech ring during subsequent practice may aid the speaker in re-learning proper speech, and/or may aid a dentist or dental design engineer in diagnosing and adjusting such appliances, such as by observing the speaker with and without use of the speech ring. When used in this context, a speech ring may be used in conjunction with conventional speech therapy devices and techniques. As another example, a speech ring as disclosed herein may be used when a speaker wishes to become more proficient at speaking a particular text, such as for an audition for stage, film, or other theatrical production, or a speaking engagement, presentation or pitch, or the like. The speaker may speak the desired text repeatedly while using a speech ring, after which the speaker's clarity and proficiency at speaking the text without the speech ring may be improved as disclosed above, relative to the clarity and proficiency prior to using the speech ring.

Figure 4A:
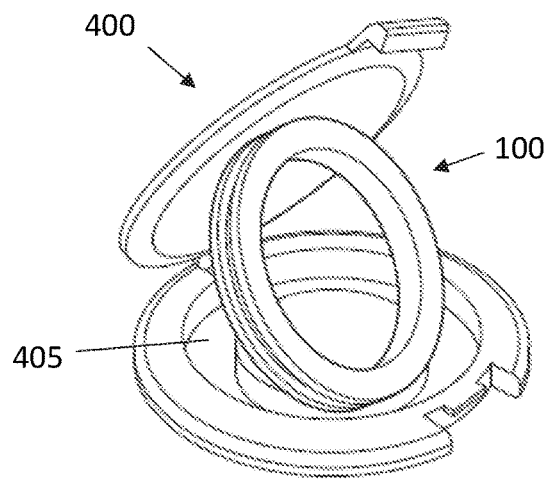
FIG. 4A shows a speech ring disposed within a case according to embodiments disclosed herein.
Figure 4B:
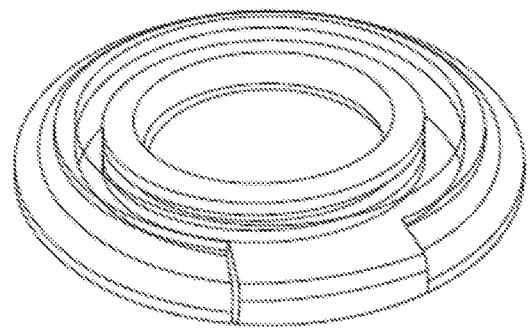
FIG. 4B shows a speech ring disposed within a case according to embodiments disclosed herein.
Figure 4C:
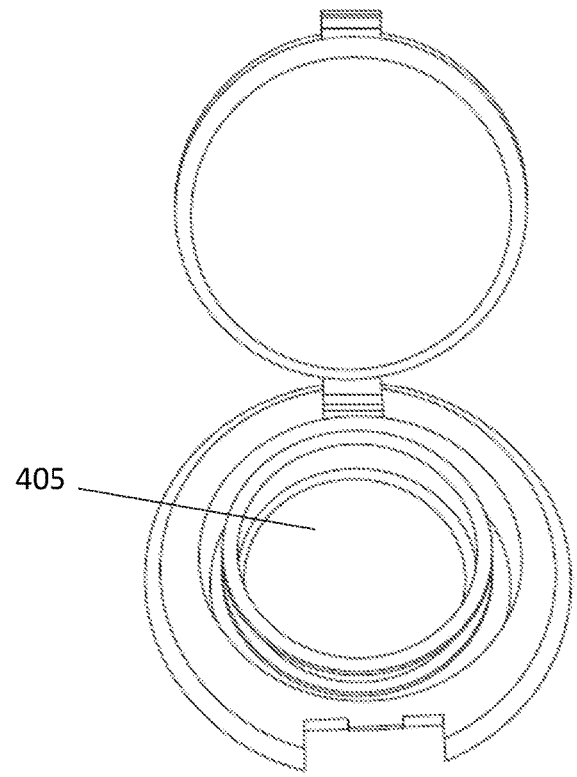
FIG. 4C shows a speech ring disposed within a case according to embodiments disclosed herein.

A speech ring as disclosed herein may be provided in a fitted case to allow for storage and protection of the device as shown in FIG. 4A-4C. FIG. 4A shows a perspective view of the ring 100 resting within the case 400, such as for display of the ring. FIG. 4B shows the ring disposed within the case, with a clear lid of the case closed over the ring. FIG. 4C shows the ring disposed within the case, with a lid of the case open. The case 400 may include a storage area 405 in which a speech ring may be placed, for example to return the ring to an original shape as previously described. The storage area may be shaped so to cause the ring to conform to an original desired shape, such as a circular shape, when the ring is placed in the case. Thus, after use by a speaker, the ring may be "reset" to its original shape due at least in part to the shape of the storage area 405 that enforces such a shape. Alternatively or in addition, the ring also may be made of a material that returns to an originally-fabricated shape, as previously disclosed. The case may be made from a rigid plastic or similar material, to prevent distortion, piercing, or other damage to the speech ring, as well as preventing the accumulation of dust or other contaminants on the speech ring.

In some embodiments, aesthetic features may be included in a speech ring as disclosed herein. For example, different colors of materials may be used and/or additives may be placed within the material or materials used to fabricate the ring. Such materials may include crushed stone, glitter, reflective chips or materials, light-reactive ("glow in the dark") materials, and the like. In some cases, such aesthetic features also may provide a functional benefit, such as where reflective or light-reactive materials increase the visibility of the ring within a speaker's mouth when the ring is being used. Such a feature may make it easier for a speech coach or similar individual to assist a speaker in determining whether the ring is being used correctly, when and/or how the ring should be used, and the like.

A speech ring as disclosed herein also may provide other benefits. For example, many people "carry" stress or tension in their jaws, such as by continuously clenching or repeatedly clenching and unclenching jaw muscles such as the masseter, grinding their teeth, or the like. A user may "re-train" these muscles to reduce clenching, and thereby reduce stress or the effects of stress, by using a speech ring as disclosed herein. It is believed that a user may improve the relaxation of the user's mouth and jaw by holding a speech ring within the user's mouth for a short period of time, such as a minute to a few minutes, each day for several consecutive days.

The foregoing description, has been described with reference to specific implementations for purpose of illustration and explanation. However, the illustrative descriptions provided herein are not intended to be exhaustive or to limit implementations of the disclosed subject matter to the precise forms disclosed. Many modifications and variations are possible in view of the teachings provided herein. The implementations provided herein are chosen and described to explain the principles of implementations of the disclosed subject matter and their practical applications, to thereby enable others skilled in the art to utilize those implementations as well as various implementations with various modifications as may be suited to the particular use contemplated.

What is claimed is:

1. A device comprising:
    a semi-rigid ring formed from one or more non-toxic materials, the semi-rigid ring comprising:
    an outer diameter in the range of 30-45 mm;
    a thickness between the outer diameter and an inner diameter of 4-5 mm; and
    a Young's modulus of at least 1 and not more than 5;
    wherein the ring assumes a deformed shape upon being placed within the mouth of a person due to pressure from the mouth of the person on the ring, and the ring returns to an original un-deformed shape after being removed from the mouth of the person.

2. The device of claim 1, wherein the ring is an ovoid torus.

3. The device of claim 2, wherein the ring has rounded edges.

4. The device of claim 1, wherein the ring is a torus having a non-regular cross section.

5. The device of claim 1, wherein the ring comprises a surface feature on the outer surface of the ring, a surface feature on the inner surface of the ring, or both.

6. The device of claim 1, wherein the ring comprises a light-reactive material.

7. The device of claim 1, wherein the ring comprises a plurality of materials.

8. The device of claim 1, wherein a portion of an outer surface of the ring less than the entire outer surface of the ring comprises a physical surface treatment different from a surface of the remainder of the outer surface of the ring.

9. The device of claim 1, wherein a portion of an inner surface of the ring less than the entire inner surface of the ring comprises a physical surface treatment different from a surface of the remainder of the inner surface of the ring.

10. A system comprising:
    a semi-rigid ring formed from one or more non-toxic materials, the semi-rigid ring comprising:
    an outer diameter in the range of 30-45 mm;
    a thickness between the outer diameter and an inner diameter of 4-5 mm; and
    a Young's modulus of at least 1 and not more than 5;
    wherein the ring assumes a deformed shape upon being placed within the mouth of a person due to pressure from the mouth of the person on the ring, and the ring returns to an original un-deformed shape after being removed from the mouth of the person; and
    a storage case comprising a storage area having dimensions sufficient to contain the ring.

11. The system of claim 10, wherein the storage area enforces an original shape of the ring when the ring is placed in the storage area.

12. The system of claim 10, wherein the storage case comprises a rigid plastic.

13. The system of claim 10, wherein the storage case comprises a closeable lid which, when closed, fully encloses the ring within the storage case.

14. A method of training the mouth of a user, the method comprising:
    placing a semi-rigid ring formed from one or more non-toxic materials in a user's mouth, the semi-rigid ring comprising:
    an outer diameter in the range of 30-45 mm; and
    a thickness between the outer diameter and an inner diameter of 4-5 mm;
    wherein the ring assumes a deformed shape upon being placed within the mouth of a person due to pressure from the mouth of the person on the ring, and the ring returns to an original un-deformed shape after being removed from the mouth of the person, and the ring is placed within the user's mouth such that the user's tongue passes freely into a center portion of the ring during speech; and
    making a plurality of speech sounds by the user while the ring is within the user's mouth.

15. The method of claim 14 further comprising:
    based upon the plurality of speech sounds made by the user while the ring is in the user's mouth, instructing the user on techniques to make the speech sounds.

16. The method of claim 15, further comprising:
    based upon the plurality of speech sounds made after the ring is removed from the user's mouth, instructing the user to repeat the process of placing the ring in the user's mouth and making the plurality of speech sounds.

\* \* \* \* \*